United States Patent [19]

Selsted

[11] Patent Number: 5,547,939
[45] Date of Patent: * Aug. 20, 1996

[54] BROAD SPECTRUM ANTIMICROBIAL COMPOUNDS AND METHODS OF USE

[75] Inventor: Michael E. Selsted, Irvine, Calif.

[73] Assignee: The Regents of the University of California, Oakland, Calif.

[ * ] Notice: The portion of the term of this patent subsequent to Jun. 28, 2011, has been disclaimed.

[21] Appl. No.: 197,205

[22] Filed: Feb. 16, 1994

Related U.S. Application Data

[63] Continuation-in-part of Ser. No. 715,271, Jun. 14, 1991, Pat. No. 5,324,716.

[51] Int. Cl.$^6$ .............. A61K 38/00; C07K 5/00; C07K 7/00; C07K 17/00
[52] U.S. Cl. .............. 514/14; 514/12; 530/324; 530/327; 426/326; 426/335; 510/382; 510/383; 422/28; 210/764; 424/405
[58] Field of Search .............. 514/14, 12; 530/324, 530/327; 426/326, 335, 332, 656; 424/404, 405; 252/89.1, 106, 173, DIG. 14; 422/28; 210/764

[56] References Cited

U.S. PATENT DOCUMENTS

| | | | |
|---|---|---|---|
| 4,543,252 | 9/1985 | Lehrer et al. | 514/12 |
| 5,324,716 | 6/1994 | Selsted et al. | 514/14 |

OTHER PUBLICATIONS

Selsted et al., *J. Biol. Chem.*, vol. 267, No. 7, Mar. 1992, pp. 4292–4295.
Smith et al., *Principles of Biochemistry*, 7th Edition, New York, pp. 32–33.
Diamond, et al., "Tracheal Antimicrobial Peptide, a Cysteine–Rich Peptide from Mammalian Tracheal Mucosa: Peptide Isolation and Cloning of A cDNA" Proc. Natl. Acad. Sci. USA 88:3952–3956 (1991).
Boman, Hans G., "Antibacterial Peptides: Key Components Needed in Immunity." Cell 65:205–207 (1991).
Zanetti et al., "Bactenecins, Defense Polypeptides of Bovine Neutrophils, are Generated from Precursor Molecules Stored in the Large Granules." J. Cell Biol. 111:1363–1371 (1990).
Selsted et al., "Purification and Antibacterial Activity of Antimicrombial Peptides of Rabbit Granulocytes." Infection and Immunity 45:150–154 (1984).
Frank, Rainer W. et al., "Amino Acid Sequences of Two Proline–rich Bactenecins." J. Biol. Chem. 265:18871–18874 (1990).
Nagalakshmi, C. et al., "Nitroso Derivatives of Harman and Norharman–Their Formation, Characterization and Mutagenicity." Chem. Abstrs. 101:492 Ab No. 22133b, (1984).
Fox, Philip C. et al., "Secretion of Antimicrobial Proteins for the Parotid Glands of Different Aged Healthy Persons." Chem Abstrs. 107:406 Ab No. 233726j, (1991).
Shimokawa, Hisatoshi et al., "Preparation of Peptides with High Tryptophas Content as Pharmaceuticals.": Chem. Abstrs. 114:406 abstract #235045e (1991).

*Primary Examiner*—Jill Warden
*Assistant Examiner*—A. M. Davenport
*Attorney, Agent, or Firm*—Campbell and Flores

[57] ABSTRACT

The present invention provides indolicidin analogs, which are tryptophan-rich peptides that have substantially the same amino acid sequence as naturally occurring indolicidin, exhibit broad spectrum antimicrobial activity and have antimicrobial selectivity as compared to naturally occurring indolicidin. The invention also provides methods of using an indolicidin analog to inhibit or prevent the survival or growth of a microorganism in an environment capable of sustaining such survival or growth. The invention provides, for example, methods of administering an effective amount of an indolicidin analog to an environment capable of sustaining the survival or growth of a microorganism.

22 Claims, 6 Drawing Sheets

BROAD SPECTRUM ANTIMICROBIAL COMPOUNDS AND METHODS OF USE

The present application is a continuation-in-part of U.S. Ser. No. 07/715,271, filed Jun. 14, 1991, now U.S. Pat. No. 5,324,716, which is incorporated herein by reference. This invention was made with Government support under Grant Nos. AI22931 and AI31696 awarded by the National Institutes of Health. The Government has certain rights in this invention.

BACKGROUND OF THE INVENTION

1. Field of the Invention

This invention relates generally to microbicidal compounds and, more particularly, to broad spectrum tryptophan-rich antimicrobial indolicidin analogs.

2. Background Information

Infectious diseases are a primary cause of morbidity and mortality in humans and animals. For example, 8 to 10 million people have been estimated to be infected with the AIDS virus with 263,000 new cases reported in 1990 alone. Many persons infected with the AIDS virus will further suffer from opportunistic infections, such as *Candida albicans*, which causes mucocutaneous fungal disease. Other microbial infections include, for example, *E. coli* diarrhea which is caused by consumption of contaminated food and drinks. This infection affects 40–50% of visitors from industrialized countries travelling to developing countries. Gonorrhea, which is caused by a gram negative bacterium, was reported in over seven hundred and fifteen thousand cases in the United States in 1990, and 3,000 to 10,000 new cases per 100,000 people are diagnosed per year in Africa.

Antibiotic-resistant strains of *E. coli* and other bacterial, viral and fungal pathogens make the treatment of many diseases difficult and expensive. Even in cases where a disease may potentially be treated by antibiotics, the unavailability of adequate storage facilities for antibiotics, especially in underdeveloped regions of the world where diseases often are endemic, results in the inability to provide effective treatment to infected populations.

In vertebrates, polymorphonuclear leukocytes, including neutrophils and granulocytes have a central role in combatting infectious disease. These white blood cells contain membrane-bound, cytoplasmic granules, which store various components of their microbicidal arsenal. Upon infection, neutrophils engulf the invading microorganisms in membrane-bound vesicles. These vesicles then fuse with the cytoplasmic granules, exposing the microorganisms to the toxic contents of the granules. One mechanism granulocytes have for killing such microorganisms consists of an array of peptides that act as naturally-occurring antibiotics. These peptides, which are generally cationic, mediate their toxicity by interacting with and permeabilizing the cell membranes of various microorganism.

A number of families of microbicidal peptides have previously been isolated from granulocytes. The bactenecins, described by Genarro et al., Infect. Immun. 57:3142–46 (1989), Romeo et al., J. Biol. Chem. 263:9573–75 (1988), and Marzari et al, Infect. Immun. 56:2193–97 (1988), are proline and arginine-rich peptides that range in size from 1600 to 8000 daltons which were identified in part by their reactivity with a monoclonal antibody raised against a granule protein extract. The bactenecins are toxic to fungi and gram negative bacteria and, to a lesser extent, to gram positive bacteria.

The defensins are a family of fifteen peptides which constitute 5% to 18% of the cellular protein in neutrophils of various species. This class of molecules has been described by Ganz et al., Eur. J. Haematol. 44:1–8 (1990), Lehrer et al., U.S. Pat. No. 4,543,252, and Selsted et al., Infect. Immun. 45:150–154 (1984). The defensin peptides consist of 29 to 34 amino acids, with four to ten of these residues being arginine. The defensins also share six conserved cysteine residues that participate in intramolecular disulfide bonds. Defensins are microbicidal to gram negative and gram positive bacteria, fungi and certain enveloped viruses.

While the availability of naturally occurring antibiotic peptides is extremely valuable for treating infectious diseases that are not otherwise amenable to treatment by synthetic antibiotics, the usefulness of bactenecins and defensins suffers from various limitations. For example, both bactenecins and defensins are immunogenic and, therefore, treatment using these compounds could potentially result in anaphylactic or delayed hypersensitivity-type responses. The defensins have also been demonstrated to exhibit substantial in vitro cytotoxicity toward mammalian cells. Furthermore, the requirement for proper disulfide bond formation can reduce the yield of active defensins synthesized since the active molecule contains three intramolecular disulfide bonds.

Thus, there exists a need for an effective microbicidal peptide that can be easily synthesized in an active form and that is effective against a broad spectrum of microorganisms and does not exhibit undesirable side effects. The present invention satisfies these needs and provides related advantages as well.

SUMMARY OF THE INVENTION

The present invention provides indolicidin analogs, which are tryptophan-rich peptides that have substantially the same amino acid sequence as naturally occurring indolicidin, exhibit broad spectrum antimicrobial activity and have antimicrobial selectivity as compared to naturally occurring indolicidin. The invention also provides methods of using an indolicidin analog to inhibit or prevent the survival or growth of a microorganism in an environment capable of sustaining the microorganism. The invention provides, for example, methods of administering an effective amount of an indolicidin analog to an environment capable of allowing the survival or growth of a microorganism.

BRIEF DESCRIPTION OF THE DRAWINGS

FIG. 1 (A–B) shows the chromatograms obtained by RP-HPLC of naturally occurring indolicidin (SEQ ID NO: 1). 1(A) Elution using water-acetonitrile solvents containing 0.1% TFA. 1(B) Elution using water-acetonitrile solvents containing 0.13% HFBA.

DETAILED DESCRIPTION OF THE INVENTION

The present invention provides indolicidin analogs, which are tryptophan-rich peptides that have substantially the same amino acid sequence as naturally occurring indolicidin (SEQ ID NO: 1), exhibit broad spectrum antimicrobial activity and have antimicrobial selectivity as compared to naturally occurring indolicidin (see Table 1). Naturally occurring indolicidin is a thirteen amino acid peptide that was named based on its tryptophan-rich nature and its microbicidal properties (see FIGS. 2 and 3). The indolicidin analogs of the present invention generally contain twelve or thirteen amino acids and, like indolicidin, are tryptophan-rich peptides. For example, the exemplified indolicidin analogs are characterized by the general structure: $H_2N$-I-L-P-W-K-W-P-W-W-P-W-X (SEQ ID NO: 8), where X designates one or two independently selected amino acids. An additional feature of indolicidin is its low immunogenicity, which is beneficial for therapeutic use as an antimicrobial compound.

Indolicidin (SEQ ID NO: 1; Table 1) and the exemplified indolicidin analogs (SEQ ID NOS: 2–7) are characterized, in part, as being tryptophan-rich peptides. As used herein, the term "tryptophan-rich peptide" means a peptide having at least about 25% of its residues consisting of tryptophan. Indolicidin, for example, has a tryptophan content of about 38 percent (5/13 residues). In nature, each amino acid occurs in proteins in a characteristic expected proportion. For example, tryptophan is the least frequently used amino acid in naturally occurring proteins, with an average occurrence of about 1 percent, whereas alanine generally represents about 9 percent of the amino acid content of a protein (Clapper, *Biochem. Biophys. Res. Comm.* 78:1018–1024 (1977)). Thus, a tryptophan-rich sequence as defined herein can be readily identified by containing a much greater proportion of tryptophan residues than would be expected based on the average occurrence of tryptophan in a protein.

Indolicidin analogs are further characterized by having substantially the same sequence as naturally occurring indolicidin. As used herein, the term "substantially the same sequence" means that the peptide sequence of an indolicidin analog is at least 60% homologous with the sequence of indolicidin (SEQ ID NO: 1). Thus, a limited number of modifications can be made to the indolicidin peptide sequence to obtain indolicidin analogs that have a desirable antimicrobial selectivity such as increased antimicrobial activity or decreased hemolytic activity as compared to naturally occurring indolicidin. For example, an indolicidin analog can have the same peptide sequence as indolicidin but can be modified, for example, by containing a C-terminal reactive group other than an amide, which is found in naturally occurring indolicidin (see, for example, SEQ ID NO: 5).

TABLE 1

SEQUENCE AND MOLECULAR MASS OF INDOLICIDIN AND INDOLICIDIN ANALOGS

| NAME | AMINO ACID SEQUENCE | SEQ ID NO: | MOL. WT.* |
|---|---|---|---|
| Indol-$R_{12}R_{13}$—$NH_2$ | $H_2N$—I—L—P—W—K—W—P—W—W—P—W—R—R—$CONH_2$ | 1** | 1907 |
| Indol-$R_{12}W_{13}$—$NH_2$ | $H_2N$—I—L—P—W—K—W—P—W—W—P—W—R—N—$CONH_2$ | 2 | 1937 |
| Indol-$K_{12}K_{13}$—$NH_2$ | $H_2N$—I—L—P—W—K—W—P—W—W—P—W—K—K—$CONH_2$ | 3 | 1851 |
| Indol-$K_{12}$—$NH_2$ | $H_2N$—I—L—P—W—K—W—P—W—W—P—W—K—$CONH_2$ | 4 | 1723 |
| Indol-$R_{12}R_{13}$—OH | $H_2N$—I—L—P—W—K—W—P—W—W—P—W—R—R—OH | 5 | 1908 |
| Indol-$R_{12}$—OH | $H_2N$—I—L—P—W—K—W—P—W—W—P—W—R—OH | 6 | 1752 |
| Indol-$R_{12}K_{13}$—OH | $H_2N$—I—L—P—W—K—W—P—W—W—P—W—R—K—$CONH_2$ | 7 | 1880 |

*theoretical (calculated) molecular weights were identical to the molecular weights as determined by mass spectrometry.
**indolicidin (naturally occurring).

Modifications to the indolicidin peptide sequence also can include, for example, additions, deletions or substitutions of amino acids, provided the indolicidin analog produced by such modifications is tryptophan-rich and has substantially the same sequence of naturally occurring indolicidin as defined herein. Examples of indolicidin analogs having such modifications are provided in Table 1. For example, indol-$K_2$-$NH_2$ (SEQ ID NO: 4) is an indolicidin analog having a deletion of R-13 and a substitution of K-12 for R-12 as compared to indolicidin, where "K" and "R" refer to the single letter code for the amino acids lysine and arginine, respectively.

As used herein, the term "amino acid" is used in its broadest sense to include naturally occurring amino acids as well as non-naturally occurring amino acids including amino acid analogs. In view of this broad definition, one skilled in the art would know that reference herein to an amino acid includes, for example, naturally occurring proteogenic (L)-amino acids, (D)-amino acids, chemically modified amino acids such as amino acid analogs, naturally occurring non-proteogenic amino acids such as norleucine, and chemically synthesized compounds having properties known in the art to be characteristic of an amino acid. As used herein, the term "proteogenic" indicates that the amino acid can be incorporated into a protein in a cell through a metabolic pathway. Furthermore, the amino acid residue at any position in an indolicidin can be independently selected. As used herein, the term "independently selected" indicates that the choice of an amino acid residue at any position in an indolicidin analog does not depend on the amino acid residue contained at any other position in the analog, provided the analog maintains its tryptophan rich character.

The choice of using, for example, an (L)- or a (D)-amino acid in an indolicidin analog can depend, in part, on the desired characteristics of the indolicidin analog. For example, the incorporation of one or more (D)-amino acids can confer increased stability on a peptide in vitro or in vivo. The incorporation of one or more (D)-amino acids also can increase or decrease the antimicrobial selectivity of the peptide as determined, for example, using the assays described in Examples II and III, below, or other well known methods for determining antimicrobial selectivity in vitro or in vivo. The construction of indolicidin analogs incorporating D-amino acids, for example, can be particularly useful when it is desirable to obtain a peptide that is stable in a cell. It also can be desirable, however, to allow the peptide to remain active for only a short period of time. In that case, the use of (L)-amino acids in the peptide can allow endogenous peptidases in a cell to digest the peptide in vivo, thereby limiting the cell's exposure to an active indolicidin analog.

Indolicidin analogs can be chemically synthesized using well known methods of peptide synthesis. Indolicidin analogs were synthesized using an automated peptide synthesizer such as an Eppendorf Synostat (Madison, Wis.) or a Milligen 9050 (Milford, Mass.) (see Example I), although manual methods of solution peptide synthesis also can be used. When automated methods of peptide synthesis were used, indolicidin analogs was synthesized on a polyethylene glycolpolystyrene (PEG-PS) graft resin and using $N^\alpha$-Fmoc amino acid derivatives. In addition, a suitable linker such as a peptide amide linker (PAL; 5-(4-Fmoc-aminomethyl-3,5-dimethoxyphenoxy)valeric acid; Fmoc is 9-fluorenylmethyloxycarbonyl; Milligen) was used to create carboxamide end groups. However, the skilled artisan would know that other resins, amino acid derivatives and methods of modifying amino acid reactive groups can be used to obtain the desired indolicidin analog.

A newly synthesized peptide can be manipulated while still attached to a resin or can be removed from the resin and then modified. Methods for modifying the N-terminus or C-terminus of a peptide are well known in the art and include, for example, amidation of the C-terminus and, if desired, acetylation of the N-terminus (see, for example, *Protein Engineering: A practical approach* (IRL Press 1992); and Bodanszky, *Principles of Peptide Synthesis* (Springer-Verlag 1984), each of which is incorporated herein by reference). Similarly, methods for modifying the reactive side chain of an amino acid are well known in the art of peptide synthesis.

Selective modification of a reactive group in a peptide also can impart desirable characteristics to an indolicidin analog and the choice of including such a modification is determined, in part, by the characteristics required of the peptide. For example, indolicidin analogs can be synthesized that have greater antimicrobial selectivity than indolicidin. As used herein, the term "antimicrobial selectivity" refers to the relative amount of antimicrobial activity of an analog as compared to its cytolytic activity against normal cells in a subject. For example, an indolicidin analog that is characterized by having antimicrobial activity that is equivalent to indolicidin but having decreased hemolytic activity as compared to indolicidin is considered to have greater antimicrobial selectivity than indolicidin. For example, the synthesis of an indolicidin analog having a deletion of a C-terminal arginine (R-13) and a substitution of R-12 with K-12 (SEQ ID NO: 4) as compared to indolicidin provides an indolicidin analog that has greater antimicrobial selectivity than indolicidin (see FIGS. 4-6 and Table 2). Additional modifications can include, for example, oxidation of the indole-containing side chains of the tryptophan residues to an indole derivative. The antimicrobial selectivity of an indolicidin analog having these or other modifications can be determined using the methods described in Examples II and III.

The indolicidin analogs of the invention are further characterized by having broad spectrum antimicrobial activity.

As used herein, the term "broad spectrum antimicrobial activity" refers to the ability of an indolicidin analog to inhibit or prevent the survival or growth of various prokaryotic and eukaryotic microorganisms including, for example, protozoans such as *Giardia lamblia*, viruses, fungi such as Cryptococcus and various genera of bacteria such as Escherichia, Salmonella and Staphylococcus. Antimicrobial activity can occur through a microbicidal or a microbistatic inhibition. As used herein, the term "microbicidal inhibition" refers to the ability of an indolicidin analog to reduce or inhibit the survival of a microorganism by killing or irreversibly damaging it, whereas the term "microbistatic inhibition" refers to the ability of an indolicidin analog to inhibit the growth of a target microorganism without killing it. An indolicidin analog having microbicidal or microbistatic inhibition can be applied to an environment that presently allows for the survival or growth of a microorganism (i.e., therapeutic treatment) or to an environment at risk of supporting such survival or growth (i.e., prevention or prophylaxis).

The invention also provides methods of using an indolicidin analog to inhibit or prevent the survival or growth of a microorganism in an environment capable of sustaining such survival or growth. As used herein, the

TABLE 2

HEMOLYTIC ASSAY OF INDOLICIDIN AND INDOLICIDIN ANALOGS

| Peptide | % Hemolysis | Solution |
|---|---|---|
| Indol-$R_{12}R_{13}$—$NH_2$* | 78.5 | saline |
|  | 2.3 | serum |
| Indol-$R_{12}W_{13}$—$NH_2$ | 66.1 | saline |
|  | 0.0 | serum |
| Indol-$K_{12}K_{13}$—$NH_2$ | 52.7 | saline |
|  | 1.5 | serum |
| Indol-$K_{12}$—$NH_2$ | 16.5 | saline |
|  | 0.0 | serum |
| Indol-$R_{12}R_{13}$—OH | 47.9 | saline |
|  | 3.0 | serum |
| Indol-$R_{12}$—OH | 81.0 | saline |
|  | 2.3 | serum |
| Indol-$R_{12}K_{13}$—OH | 78.5 | saline |
|  | 2.3 | serum |

*indolicidin (naturally occurring).

term "environment capable of sustaining survival or growth of a microorganism" refers to a fluid, substance or organism where microorganisms can live. In view of the broad range of environments that allow the survival or growth of microorganisms and the disclosed effectiveness of the claimed indolicidin analogs against a broad spectrum of microorganisms, the range of "environments" encompassed by this term is necessarily broad and includes, for example, a tissue or bodily fluid of an organism such as a human, a liquid such as water or an aqueous solution, food such as a food crop, a food product or a food extract or an object such as a solid surface of an instrument used, for example, to prepare food or perform surgery.

The invention also provides a method of reducing or preventing the survival or growth of a microorganism in an environment capable of sustaining such survival or growth. The method includes administering to the environment an effective amount of an indolicidin analog having antimicrobial activity. The indolicidin analogs can be used in a variety of procedures for treating or preventing the survival or growth of microorganisms, including the microbicidal inhibition of survival of a microorganism as well as the microbistatic inhibition of growth.

An indolicidin analog can be used as a therapeutic agent, a food preservative, a disinfectant or a medicament. For example, an indolicidin analog can be used as an antibacterial, antifungal or antiviral therapeutic agent. For use as a therapeutic agent, a pharmaceutical composition can be administered to a human or animal subject. Such a composition generally will comprise an indolicidin analog having a desirable antimicrobial selectivity contained in a pharmaceutically acceptable carrier such as water, sodium phosphate buffer, phosphate buffered saline, normal saline or Krebs' ringers solution. Moreover, the pharmaceutical composition can contain other agents that can be beneficial to a treatment. For example, the composition can contain divalent cations such as calcium and magnesium, which inhibit the defensin antimicrobial peptides, but do not inhibit the antimicrobial properties of indolicidin analogs. Thus, divalent cations can be included in the pharmaceutical composition if the addition of such cations is beneficial to a therapeutic treatment. Other compounds or compositions can also be administered in conjunction with indolicidin peptides to further increase their antimicrobial properties. For example, indolicidin peptides can be administered in conjunction with bactenecins, defensins or antibiotics. Compounds such as EDTA, which disrupts microbial membranes, can be included as well. In addition, agents that facilitate uptake of the analog in a patient or stabilize the analog can be included in the pharmaceutical composition.

A pharmaceutical composition comprising an indolicidin analog can be administered to a subject by various routes such as intravenous, subcutaneous, intramuscular or intraperitoneal injection, orally or in the form of an aerosol spray. In addition, an indolicidin analog can be encapsulated in a liposome or formulated as a non-liposome lipid complex comprising a lipid and an indolicidin analog and administered to a subject. The skilled artisan can select a specific route and method of administration based, for example, on the location of a microorganism in a subject, the particular characteristics of the microorganism and the specific indolicidin analog that is administered.

Food and food products also can be treated using indolicidin analogs for the purpose of preserving the food or eliminating potential microorganisms. For example, shellfish and poultry products routinely harbor enteric pathogenic microorganisms that can cause severe human disease. Such microorganisms can be eliminated by treatment with an indolicidin analog. Food crops such as fruits, vegetables and grains also can be treated with an indolicidin analog in order to reduce or eliminate post-harvest spoilage caused by microorganisms. In this case, the indolicidin analog can be administered topically using, for example, an aerosolized form of the analog. Alternatively, where the analog to be administered is a simple, chemically unmodified peptide, administration can be via transgenic expression of the recombinant indolicidin analog. Methods for constructing an appropriate vector and effecting transgenic expression of a peptide are well known in the art (see, for example, Sambrook et al., *Molecular Cloning.: A laboratory manual* (Cold Spring Harbor Laboratory Press 1989), which is incorporated herein by reference).

An indolicidin analog also can be used as a disinfectant to sterilize an object or solution and, thereby, prevent the survival or growth of a microorganism on the object or in the solution. An indolicidin analog can be used essentially on any object or in any solution where the survival or growth of microorganisms is undesirable including an object or solution that comes into contact with a mammal such as a human. Examples of such objects include baby wipes, diapers, bandaids, towelettes, make-up products and eyewash and contact lens solutions. For these uses, an indolicidin analog can be applied topically to the object or can be added to the solution.

Figure 4:
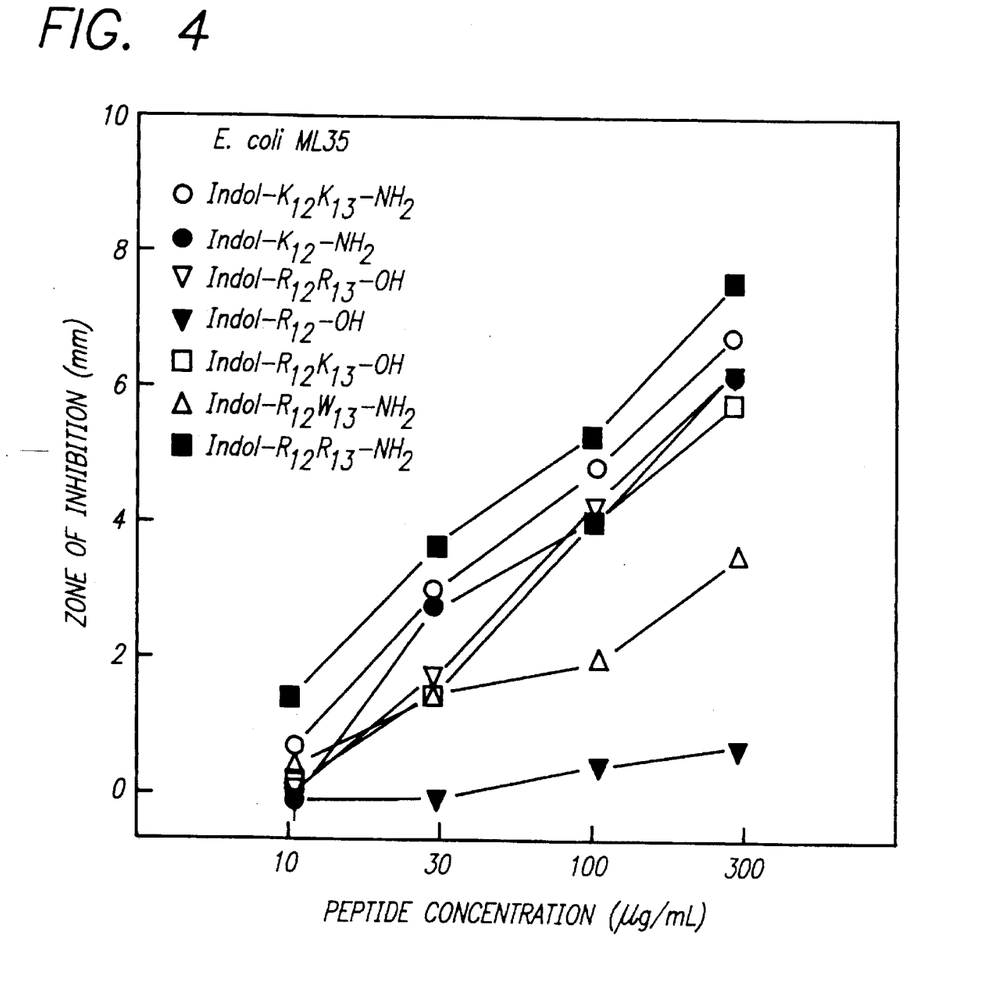
FIG. 4 compares the antimicrobial activity of indolicidin with various indolicidin analogs against *E. coli* ML35. Structures of the indolicidin analogs are shown in Table 1.
Figure 5:
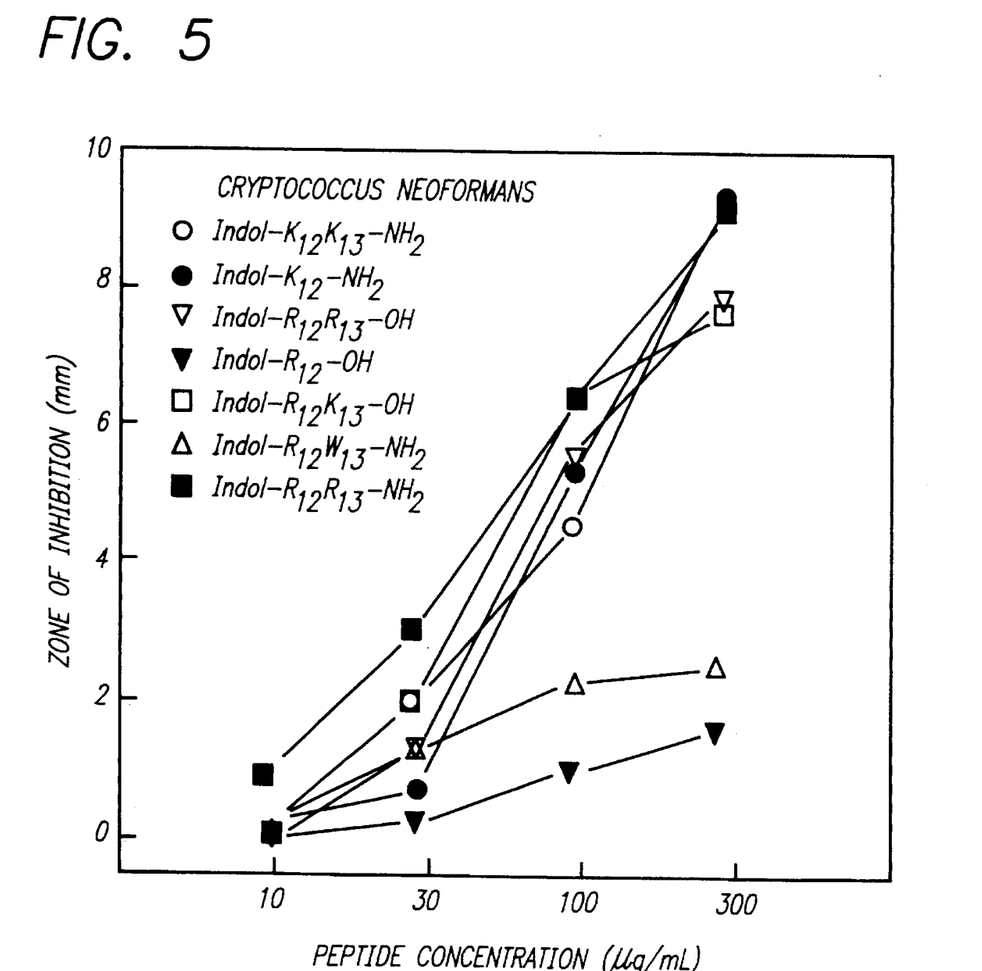
FIG. 5 compares the antimicrobial activity of indolicidin with various indolicidin analogs against *C. neoformans*. Structures of the indolicidin analogs are shown in Table 1.
Figure 6:
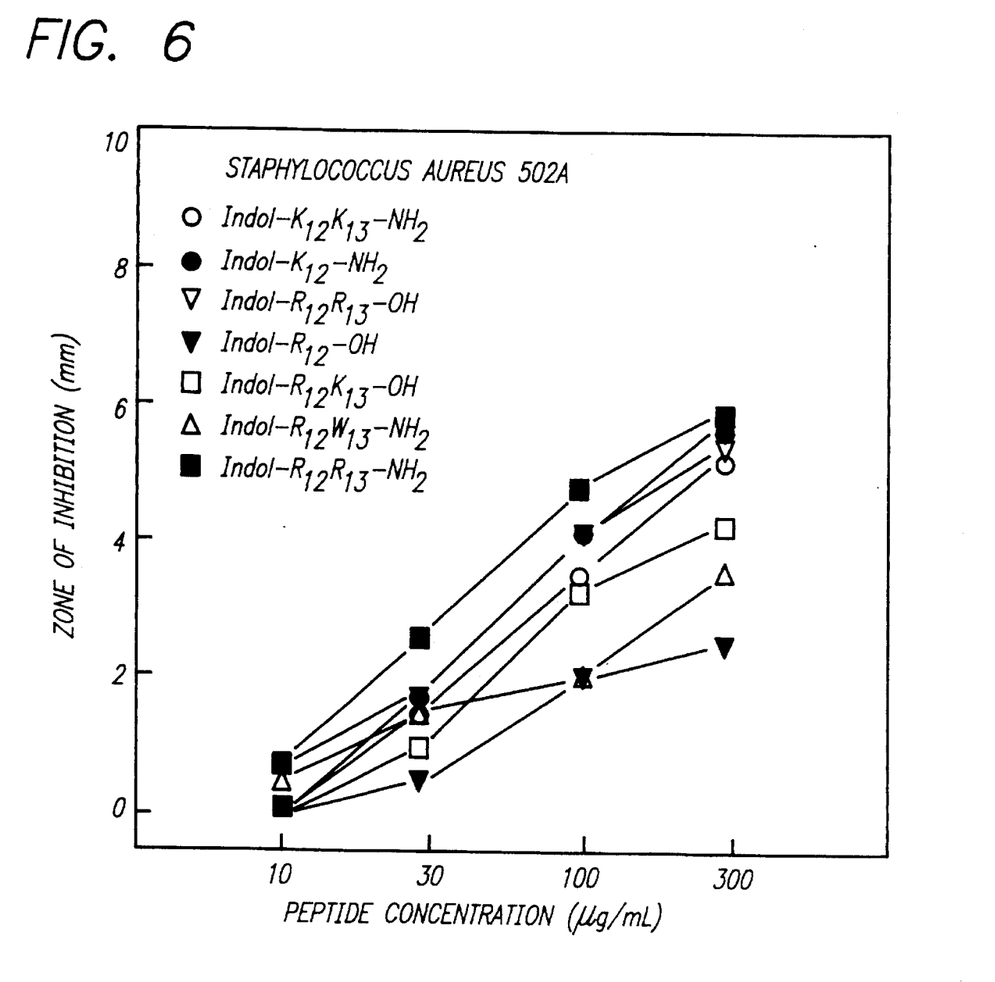
FIG. 6 compares the antimicrobial activity of indolicidin with various indolicidin analogs against *S. aureus* 502a. Structures of the indolicidin analogs are shown in Table 1.

In order to exhibit antimicrobial activity in an environment, an effective amount of an indolicidin analog must be administered. As used herein, the term "effective amount" refers to amount of an indolicidin analog that reduces or inhibits the survival or growth of a microorganism in an environment without producing a harmful effect to the environment such as unacceptable hemolytic activity when administered, for example, to a human. An effective amount will vary depending, for example, on the characteristics of the target microorganism, the extent of prior infection or growth, the particular environment and the specific indolicidin analog administered. An effective amount of an indolicidin analog can be determined using the methods described in Examples II and III or otherwise known in the art and typically is about 0.5 and 500 µg/ml to inhibit, for example, the growth of *E. coli* (FIG. 4; see, also, FIGS. 5 and 6).

The following examples are intended to illustrate but not limit the invention.

EXAMPLE I

Synthesis and Characterization of Indolicidin Analogs

This example demonstrates methods for synthesizing and characterizing the indolicidin analogs.

Indolicidin can be purified from bovine neutrophil granules as described in detail in U.S. Ser. No. 07/715,271, filed Jun. 14, 1991, or can be chemically synthesized. Indolicidin analogs were chemically synthesized using Fmoc chain assembly on either an Eppendorf Synostat or Milligen 9050 automated peptide synthesizer. Amino acid derivatives were activated in situ using BOP/HOBt (benzotriazolyl N-oxytris(dimethylamino)phosphonium hexafluorophosphate/1-hydroxybenzotriazole; Milligen; Advanced Chemtech) in the presence of N-methylmorpholine (1:1:1:2). Fmoc-PAL-polystyrene (PS) resin was used to synthesize peptides having a C-terminal amide and Fmoc-Arg(Pmc)-PS resin or Fmoc-Lys(tBoc)-PS resin was used to synthesize peptides having a free acid C-terminus. Arginine and lysine residues were protected with Pmc (2,2,5,7,8-pentamethylchroman-6-sulfonyl) and tBoc (tertbutyloxycarbonyl), respectively (Milligen; Advanced Chemtech).

Fmoc syntheses of indolicidin performed at a 2.8 mmol scale and the indolicidin analogs were assembled at a 0.2 mmol scale. Newly synthesized indolicidin or indolicidin analogs were released from the solid support by treatment for 4 hr with reagent K (TFA (trifluoroacetic acid):thioanisole: ethanedithiol:phenol:water) (82.5:5:2.5:5:5), then diluted with 30% acetic acid, extracted with dichloromethane and purified to homogeneity by reverse phase-high performance liquid chromatography (RP-HPLC) as described in U.S. Ser. No. 07/715,271.

Figure 1A:
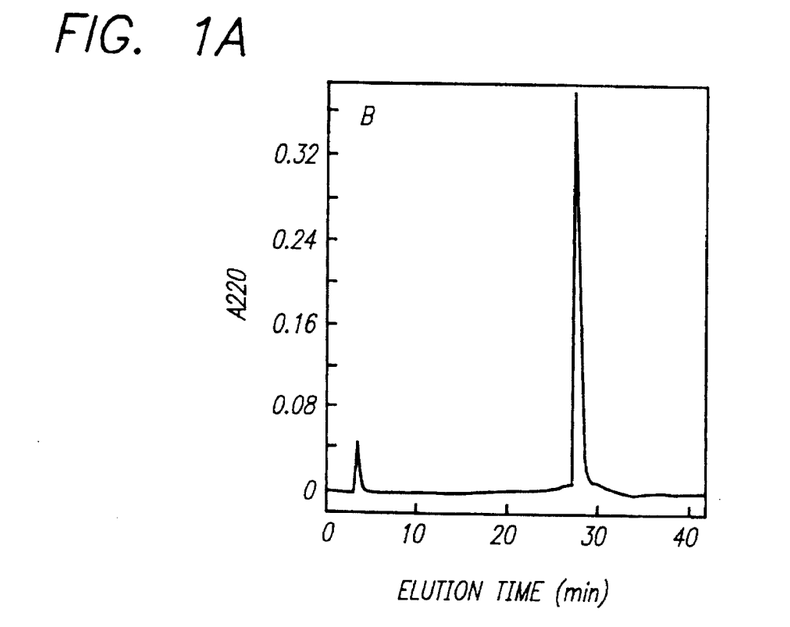

Purity of the peptides was confirmed by analytical RP-HPLC. In one protocol, the peptides were analyzed on a 0.4×25 cm Vydac C-18 column using water-acetonitrile solvents containing 0.1% TFA. Ten µg of peptide was chromatographed at 1 ml/min using a 20% to 40% acetonitrile gradient developed over 20 minutes. As shown in FIG. 1.A., indolicidin elutes as a single peak. Similar results were obtained with the various indolicidin analogs (not shown).

Figure 1B:
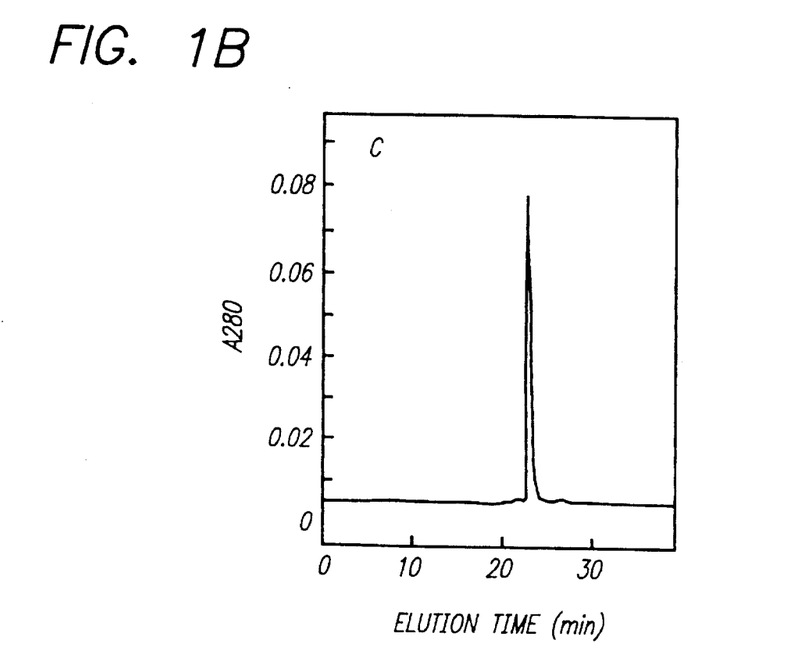

In a second protocol, the peptides were analyzed on a 1×25 cm Vydac C-18 column using water-acetonitrile solvents containing 0.13% heptafluorobutyric acid (HFBA). Ten µg of peptide was chromatographed at 1 ml/min using a 30% to 60% gradient developed over thirty minutes.

Again, indolicidin (FIG. 1.B.) and the indolicidin analogs (not shown) eluted as a single peak.

Purity of indolicidin and the indolicidin analogs was further confirmed by acid-urea polyacrylamide gel electrophoresis (PAGE) on a 12.5% gel (see, for example, Selsted, in *Genetic Engineering*, Vol. 15, pages 131–147 (Plenum Press, NY 1993), which is incorporated herein by reference. For each peptide, a single band that migrated to the expected position based on the predicted molecular weight and net charge of the peptides was observed following Coomassie blue staining (not shown).

The mass of each peptide was determined by electrospray fast atom bombardment mass spectrometry (MS) as described by Fenn et al., *Science* 246:64–71 (1989), using a JEOL HX100 HF double focussing magnetic sector mass spectrometer operating at a five kilovolt acceleration potential with a nominal resolution setting of 3000. Lyophilized peptide was dissolved in 5% acetic acid and applied to a stainless steel stage. A 6 keV beam of xenon atoms was used to ionize the sample. Spectra were collected and mass was assigned in real time using a JEOL DA5000 data system. As indicated in Table 1, the monoisotopic mass of each peptide as experimentally measured by MS precisely matched the expected theoretical mass.

The peptides also were characterized by amino acid analysis of phenylthiocarbamyl derivatives measured in vapor phase hydrochloric acid (HCl) hydrolysates (24 hr at 110 ° C.) as described by Bidlingmeyer et al. (*J. Chromatogr.* 336:93–104 (1984), which is incorporated herein by reference). Five µg of peptide was hydrolyzed in boiling HCl. Following hydrolysis, HCl was removed under vacuum and the hydrolyzed sample was derivatized by adding ethanol:triethylamine:water:phenylisothiocyanate (7:1:1:1). The samples were incubated for 20 min at room temperature and the relative amounts of derivatized amino acids were determined by analytical RP-HPLC. Tryptophan was determined spectrophotometrically by analyzing a peptide in 6M guanidine hydrochloride, 20 mM sodium phosphate (pH 6.5), as described by Edelhoch, (*Biochemistry* 6:1948–1954 (1967), which is incorporated herein by reference). The results of the amino acid analyses indicated that each of the peptides contained the expected relative amino acid composition.

The sequence of indolicidin and each of the indolicidin analogs was confirmed by automated amino acid sequence analysis using an ABI Model 475A instrument (Applied Biosystems, Inc., Foster City, Calif.). The amino acid sequence of indolicidin and each of the analogs is shown in Table 1.

The structures determined for indolicidin and the indolicidin analogs are shown in Table 1 (SEQ ID NOS: 1–7). The structure of indolicidin confers extremely low immunogenicity properties on the peptide, as five attempts to raise antibodies to indolicidin were unsuccessful.

EXAMPLE II

Antimicrobial Activity of Indolicidin Analogs

This example demonstrates the broad spectrum antimicrobial activity of indolicidin analogs.

The time course and dose-dependence of the antimicrobial activity of an indolicidin analog can be determined by incubating a microorganism with the analog and determining the viability after various times of incubation or after treatment with various concentrations of the analog. Assays were performed in 10 mM sodium phosphate buffer, pH 7.4, at 37° C., as described by Selsted et al. (*Infect. Immun.* 45:150–154 (1985), which is incorporated herein by reference).

Figure 2:
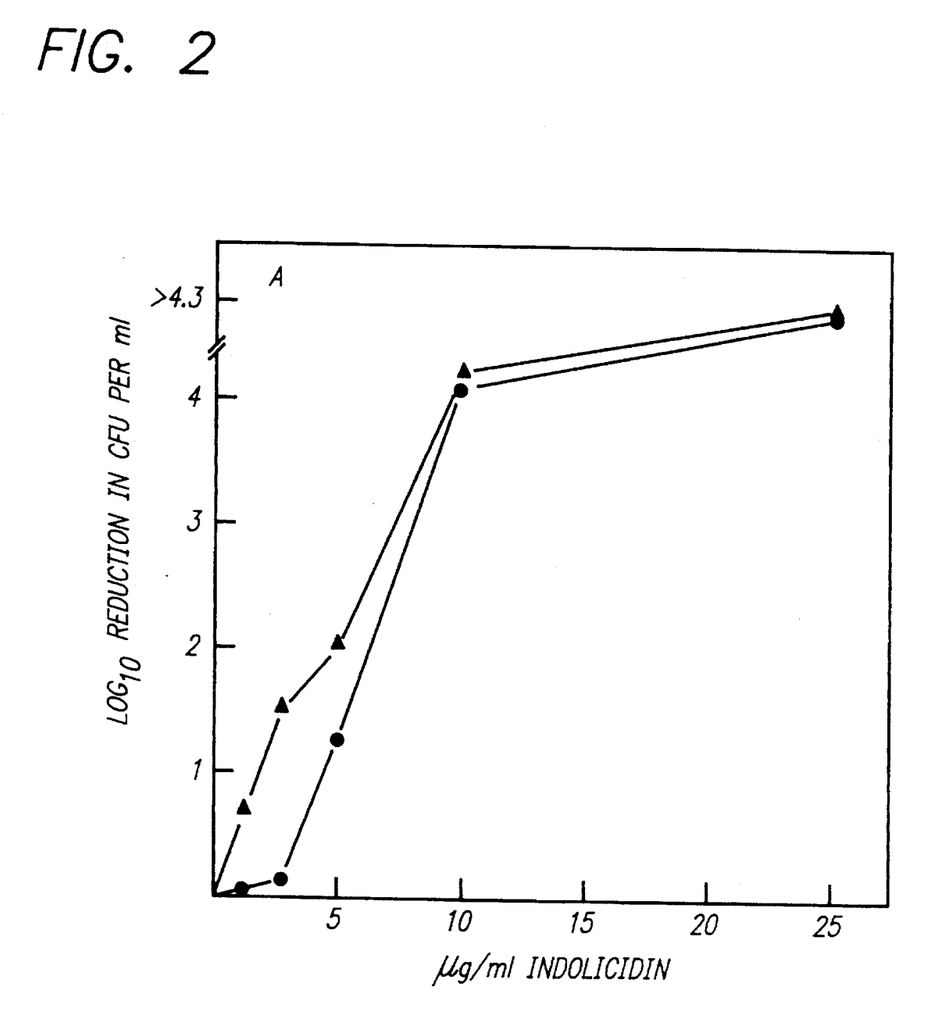
FIG. 2 demonstrates the antimicrobial activity of indolicidin. *E. coli* ML-35 (▲) or *S. aureus* (●) were incubated for 2 hr with 0 to 25 µg/ml of indolicidin. Killing is expressed as the $\log_{10}$ reduction in colony forming units (CFU) compared to the control incubation, which contained buffer and an appropriate volume of the indolicidin diluent, 0.01% acetic acid.

The dose response of a gram negative bacterial strain, *Escherichia coli* ML35, and a gram positive bacterial strain, Staphylococcus aureus 502A, to indolicidin was determined by incubating $2 \times 10^6$ colony forming units (CFU) of log phase bacteria with 0–25 ug/ml of indolicidin for two hours. Following incubation, the cultures were serially diluted and plated on nutrient agar. As shown in FIG. 2, viability of both gram negative and gram positive bacteria was reduced by at least four orders of magnitude in incubations containing 10 ug/ml of indolicidin. *E. coli* was more susceptible than *S. aureus*, as >95% of the input cells were killed after 2 hr incubation with 2.5 ug/ml indolicidin. The indolicidin diluent, 0.01% acetic acid, had no effect on either bacterial strain.

Figure 3:
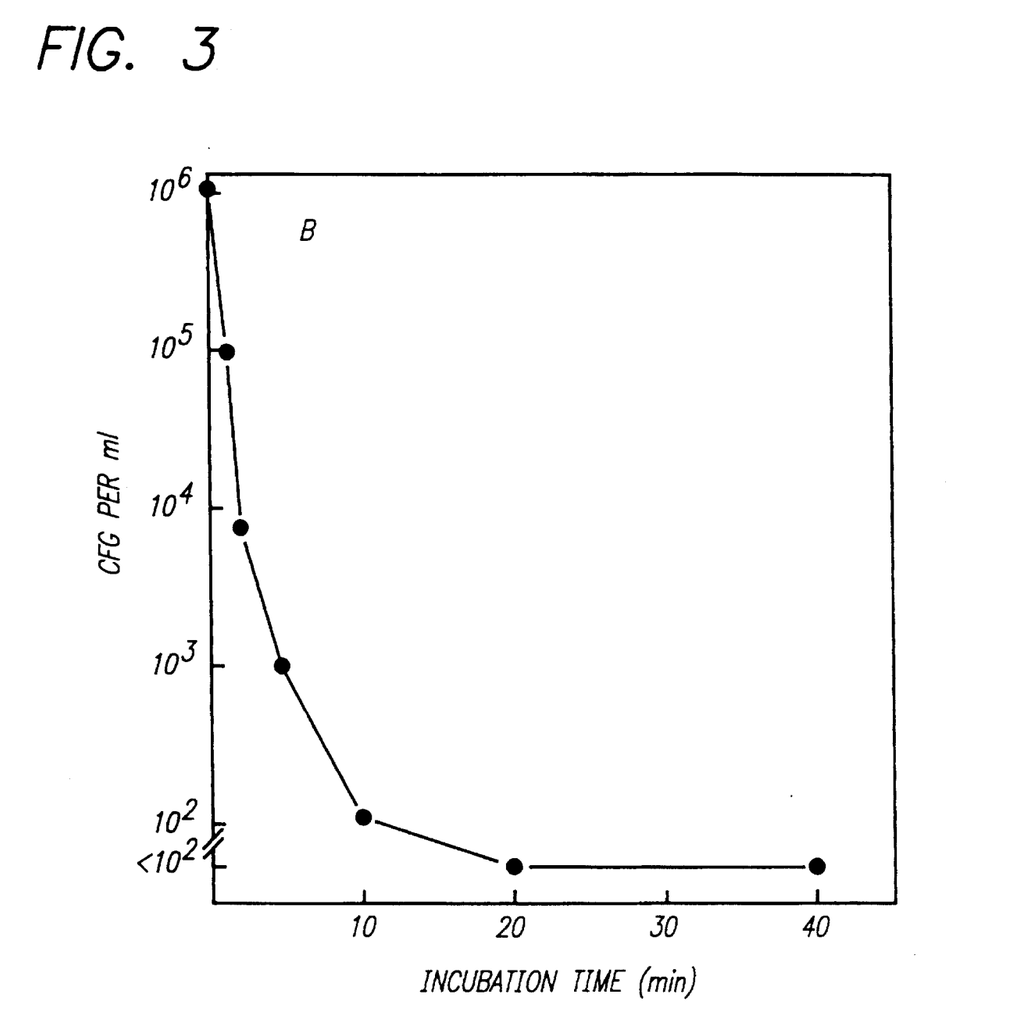
FIG. 3 demonstrates the microbicidal kinetics of indolicidin following incubation of *E. coli* with 25 µg/ml of indolicidin for various times up to 40 minutes.

The kinetics of indolicidin antimicrobial activity was evaluated by incubating $2 \times 10^6$ *E. coli* with 25 ug/ml of indolicidin for 1–40 min. Following incubation for the appropriate time, an aliquot of the culture was removed and diluted and plated as described above. As shown in FIG. 3, 25 µg/ml indolicidin reduced the number of *E. coli* CFU by three orders of magnitude within 5 min and the culture essentially was sterilized after 20 min.

The broad spectrum antimicrobial activity of indolicidin and indolicidin analogs also was determined using a gram negative bacterial strain, *Escherichia coli* ML35, a gram positive bacterial strain, *Staphylococcus aureus* 502A, and a fungus, *Cryptococcus neoformans*, in an agar diffusion assay, essentially as described by Hultmark et al., *EMBO J.* 2:571–576 (1983) as modified by Lehrer et al., *J. Immunol. Meth.* 137:167–173. Briefly, nutrient-containing agar (or agarose) plates were seeded with a selected target microorganism and 5–10 µl of peptide was placed into a well formed in the solid medium or onto a disc placed on the surface of the medium. Following an appropriate incubation interval, microbial growth inhibition was visualized and quantitated by measuring the clear zone around each well or disc (see, also, Selsted, 1993).

As shown in FIGS. 4–6, indolicidin (indol-$R_{12}R_{13}$-$NH_2$; SEQ ID NO: 1) had the greatest antimicrobial activity against the microorganisms tested. Two of the indolicidin analogs, indol-$R_{12}$-OH (SEQ ID NO: 6) and indol-$R_{12}W_{13}$-$NH_2$ (SEQ ID NO: 2) were markedly less potent than indolicidin and the remaining analogs were about as potent as indolicidin or slightly less potent. The results indicate that antimicrobial activity is not greatly reduced by substituting lysine for arginine at positions 12 and 13 of indolicidin. The results further indicate that the most active peptides were amidated and/or possess a dibasic dipeptide at the C-terminus.

EXAMPLE III

Hemolytic Activity of Indolicidin Analogs

This example demonstrates the cytolytic potential toward normal cells induced by indolicidin analogs.

The hemolytic activity of each peptide was examined using an erythrocyte lysis assay. An 8% (vol:vol) erythrocyte suspension in normal saline or in 80% mouse serum was incubated with 30 µg peptide. After 18 hr incubation at 37° C. intact erythrocytes were removed by centrifugation and the $A_{550}$ of the supernatant was determined as a measure of hemolysis. As a control (100% lysis), supernatant was collected from an erythrocyte suspension treated with 1% NP40 detergent.

As summarized in Table 2, indolicidin had the greatest hemolytic activity when the assay was performed in saline. One peptide, indol-$K_{12}NH_2$ (SEQ ID NO: 4), had very little hemolytic activity. Mouse serum abrogated nearly all of the hemolytic activity of each peptide. These results demonstrate that indolicidin analogs such as indol-$K_{12}NH_2$ (SEQ ID NO: 4) can be obtained that have greater antimicrobial selectivity than indolicidin.

Although the invention has been described with reference to the presently-preferred embodiment, it should be understood that various modifications can be made by those skilled in the art without departing from the invention. Accordingly, the invention is limited only by the claims.

I claim:

1. An indolicidin analog having the amino acid sequence:

$H_2N$-I-L-P-W-K-W-P-W-W-P-W-X     (SEQ ID NO: 8), wherein X is one or two independently selected amino acids, said indolicidin analog having a c-terminal reactive group.

2. The indolicidin analog of claim 1, wherein said c-terminal reactive group is a C-terminal amide.

3. The indolicidin analog of claim 1, wherein said analog has antimicrobial activity against microorganisms selected from the group consisting of gram positive bacteria, gram negative bacteria, protozoans, yeast, fungi and viruses.

4. The antimicrobial compound of claim 3, wherein said microorganisms are selected from the group consisting of Staphylococcus aureus, Escherichia coli, Candida albicans, Salmonella typhimurium, Cryptococcus neoformans and Giardia lamblia.

5. An indolicidin analog selected from the group consisting of:

| | |
|---|---|
| $H_2N$—I—L—P—W—K—W—P—W—W—P—W—R—W—$CONH_2$ | (SEQ ID NO: 2) |
| $H_2N$—I—L—P—W—K—W—P—W—W—P—W—K—K—$CONH_2$ | (SEQ ID NO: 3) |
| $H_2N$—I—L—P—W—K—W—P—W—W—P—W—K—$CONH_2$ | (SEQ ID NO: 4) |
| $H_2N$—I—L—P—W—K—W—P—W—W—P—W—R—R—OH | (SEQ ID NO: 5) |
| $H_2N$—I—L—P—W—K—W—P—W—W—P—W—R—OH | (SEQ ID NO: 6) and |
| $H_2N$—I—L—P—W—K—W—P—W—W—P—W—R—K—$CONH_2$ | (SEQ ID NO: 7) |

6. An indolicidin analog having the amino acid sequence of SEQ ID NO: 4.

7. A method of microbicidal inhibition or microbistatic inhibition of survival or growth of a microorganism in an environment capable of sustaining survival or growth of the microorganism, comprising administering to said environment a microbicidally or microbistatically effective amount of the indolicidin analog of claim 1.

8. The method of claim 7, wherein said c-terminal reactive group is a C-terminal amide.

9. The method of claim 8, wherein said analog comprises the peptide of SEQ ID NO: 4.

10. The method of claim 7, wherein said antimicrobial activity is against a microorganism selected from the group consisting of gram positive bacteria, gram negative bacteria, protozoans, yeast, fungi and viruses.

11. The method of claim 10, wherein said microorganisms are selected from the group consisting of *Staphylococcus aureus, Escherichia coli, Candida albicans, Salmonella typhimurium, Cryptococcus neoformans* and *Giardia lamblia*.

12. The method of claim 7, wherein said environment is a food or food product.

13. The method of claim 7, wherein said environment is an aqueous solution.

14. The method of claim 7, wherein said environment is an inanimate object comprising a surface.

15. The method of claim 7, wherein said environment is a mammal.

16. The method of claim 7, wherein said effective amount is between about 0.5 and 500 µg/ml final concentration.

17. The method of claim 7, wherein said administration is topical.

18. The method of claim 7, wherein said administration is via injection.

19. The method of claim 7, wherein said administration is oral.

20. A pharmaceutical composition comprising an effective amount of the indolicidin analog and a pharmaceutically acceptable carrier.

21. The pharmaceutical composition of claim 20, wherein said pharmaceutically acceptable carrier is a liposome.

22. The pharmaceutical composition of claim 20, wherein said pharmaceutically acceptable carrier is a non-liposome lipid complex.

* * * * *

UNITED STATES PATENT AND TRADEMARK OFFICE
CERTIFICATE OF CORRECTION

PATENT NO. : 5,547,939
DATED : Aug. 20, 1996
INVENTOR(S) : Michael E. Selsted

It is certified that error appears in the above-identified patent and that said Letters Patent is hereby corrected as shown below:

In column 4, line 37, please delete "$K_2$-$NH_2$" and replace therefor --$K_{12}$-$NH_2$--.

At claim 20, column 16, line 10, please delete "the indolicidin analog" and insert therefor --the indolicidin analog of claim 1--.

Signed and Sealed this

Twenty-seventh Day of February, 2001

Attest:

NICHOLAS P. GODICI

Attesting Officer    *Acting Director of the United States Patent and Trademark Office*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( D ) TOPOLOGY: linear     ( x i ) SEQUENCE DESCRIPTION: SEQ ID NO:1:

Ile  Leu  Pro  Trp  Lys  Trp  Pro  Trp  Trp  Pro  Trp  Arg  Arg
    1                      5                                10

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( D ) TOPOLOGY: linear     ( x i ) SEQUENCE DESCRIPTION: SEQ ID NO:2:

Ile  Leu  Pro  Trp  Lys  Trp  Pro  Trp  Trp  Pro  Trp  Arg  Trp
    1                      5                                10

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( D ) TOPOLOGY: linear     ( x i ) SEQUENCE DESCRIPTION: SEQ ID NO:3:

Ile  Leu  Pro  Trp  Lys  Trp  Pro  Trp  Trp  Pro  Trp  Lys  Lys
    1                      5                                10

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( D ) TOPOLOGY: linear     ( x i ) SEQUENCE DESCRIPTION: SEQ ID NO:4:

Ile  Leu  Pro  Trp  Lys  Trp  Pro  Trp  Trp  Pro  Trp  Lys
    1                      5                                10

( 2 ) INFORMATION FOR SEQ ID NO:5:

( i ) SEQUENCE CHARACTERISTICS:
        ( A ) LENGTH: 13 amino acids
        ( B ) TYPE: amino acid
        ( D ) TOPOLOGY: linear     ( x i ) SEQUENCE DESCRIPTION: SEQ ID NO:5:

```
Ile Leu Pro Trp Lys Trp Pro Trp Trp Pro Trp Arg Arg
1             5                   10
```

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( D ) TOPOLOGY: linear     ( x i ) SEQUENCE DESCRIPTION: SEQ ID NO:6:

```
Ile Leu Pro Trp Lys Trp Pro Trp Trp Pro Trp Arg
1             5                   10
```

( 2 ) INFORMATION FOR SEQ ID NO:7:

( i ) SEQUENCE CHARACTERISTICS:
        ( A ) LENGTH: 13 amino acids
        ( B ) TYPE: amino acid
        ( D ) TOPOLOGY: linear     ( x i ) SEQUENCE DESCRIPTION: SEQ ID NO:7:

```
Ile Leu Pro Trp Lys Trp Pro Trp Trp Pro Trp Arg Lys
1             5                   10
```

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( D ) TOPOLOGY: linear     ( i x ) FEATURE:
        ( A ) NAME/KEY: Peptide
        ( B ) LOCATION: 12
        ( D ) OTHER INFORMATION: /note="Xaa =one or two
        independently selected amino acids."

( x i ) SEQUENCE DESCRIPTION: SEQ ID NO:8:

```
Ile Leu Pro Trp Lys Trp Pro Trp Trp Pro Trp Xaa
1             5                   10
```